US011527304B2

(12) United States Patent
Kaseniit et al.

(10) Patent No.: US 11,527,304 B2
(45) Date of Patent: Dec. 13, 2022

(54) SYSTEMS AND METHODS FOR INFERRING GENETIC ANCESTRY FROM LOW-COVERAGE GENOMIC DATA

(71) Applicant: MYRIAD WOMEN'S HEALTH, INC., South San Francisco, CA (US)

(72) Inventors: Kristjan Eerik Kaseniit, South San Francisco, CA (US); Imran Saeedul Haque, South San Francisco, CA (US)

(73) Assignee: MYRIAD WOMEN'S HEALTH, INC., South San Francisco, CA (US)

( * ) Notice: Subject to any disclaimer, the term of this patent is extended or adjusted under 35 U.S.C. 154(b) by 656 days.

(21) Appl. No.: 16/523,674

(22) Filed: Jul. 26, 2019

(65) Prior Publication Data

US 2019/0348147 A1 Nov. 14, 2019

Related U.S. Application Data

(63) Continuation of application No. PCT/US2017/065657, filed on Dec. 11, 2017.

(60) Provisional application No. 62/452,617, filed on Jan. 31, 2017.

(51) Int. Cl.
| | | |
|---|---|---|
| G01N 33/48 | (2006.01) | |
| G16B 20/20 | (2019.01) | |
| G16B 10/00 | (2019.01) | |
| G16B 30/00 | (2019.01) | |

(52) U.S. Cl.
CPC ............ *G16B 20/20* (2019.02); *G16B 10/00* (2019.02); *G16B 30/00* (2019.02)

(58) Field of Classification Search
None
See application file for complete search history.

(56) References Cited

U.S. PATENT DOCUMENTS

| | | |
|---|---|---|
| 2010/0086926 A1 | 4/2010 | Craig |
| 2010/0332474 A1 | 12/2010 | Birdwell |
| 2014/0304270 A1 | 10/2014 | Torkamani |
| 2016/0048634 A1 | 2/2016 | Torkamani |
| 2016/0098519 A1 | 4/2016 | Zwir |
| 2016/0171155 A1 | 6/2016 | Do |

FOREIGN PATENT DOCUMENTS

| | | |
|---|---|---|
| WO | 2016089920 | 6/2016 |

OTHER PUBLICATIONS

Frichot, Eric, et al. "Fast and efficient estimation of individual ancestry coefficients." Genetics 196.4 (2014): 973-983.*
Alexander et al., "Fast model-based estimation of ancestry in unrelated individuals", Genome Res. Sep. 2009;19(9):1655-64. doi: 10.1101/gr.094052.109. Epub Jul. 31, 2009.
Engelhardt et al., "Analysis of population structure: a unifying framework and novel methods based on sparse factor analysis", PLoS Genet. Sep. 16, 2010;6(9):e1001117. doi: 10.1371/journal.pgen.1001117.
Frichot et al., "Fast Inference of Admixture Coefficients Using Sparse Non-negative Matrix Factorization Algorithms", arXiv, Sep. 24, 2013, pp. 1-31.
International Search Report and Written Opinion issued in PCT/US2017/065657 dated Mar. 5, 2018 (19 pages).
Libiger et al., "A Method for Inferring an Individual's Genetic Ancestry and Degree of Admixture Associated with Six Major Continental Populations", Front Genet. Jan. 14, 2013;3:322. doi: 10.3389/fgene.2012.00322. eCollection 2012.
Marchiela et al., "One thousand genomes imputation in the National Cancer Institute Breast and Prostate Cancer Cohort Consortium aggressive prostate cancer genome-wide association study", Prostate. May 2013;73(7):677-89. doi: 10.1002/pros.22608. Epub Dec. 19, 2012.
Marchini et al., "Genotype imputation for genome-wide association studies", Nat Rev Genet. Jul. 2010;11(7):499-511. doi: 10.1038/nrg2796.
Rosenberg et al., "Clines, clusters, and the effect of study design on the inference of human population structure", PLoS Genet. Dec. 2005;1(6):e70. Epub Dec. 9, 2005.

* cited by examiner

*Primary Examiner* — Anna Skibinsky
(74) *Attorney, Agent, or Firm* — Foley & Lardner LLP (57) ABSTRACT

A computer-implemented method for inferring genetic ancestry from low-coverage genomic data may include (i) generating a reference matrix representing a genetic reference panel in terms of dosages for given reference samples at given loci, (ii) decomposing the reference matrix via non-negative matrix factorization into an ancestral genotype matrix and an ancestral attribution matrix, (iii) resampling the reference matrix, (iv) deriving an ancestral alternate reads matrix that, when multiplied with the ancestral attribution matrix, approximates the resampled reference matrix, (v) deriving an ancestral attribution vector that, when multiplied with the ancestral alternate reads matrix, approximates a vector representing the test sample, and (vi) determining the genetic ancestry of the subject based on the ancestral attribution vector. Various other methods, systems, and computer-readable media are also disclosed.

21 Claims, 6 Drawing Sheets

SYSTEMS AND METHODS FOR INFERRING GENETIC ANCESTRY FROM LOW-COVERAGE GENOMIC DATA

CROSS-REFERENCE TO RELATED APPLICATIONS

This application is a continuation of International Patent Application No. PCT/US2017/065657, filed Dec. 11, 2017, which claims priority to U.S. Provisional Application No. 62/452,617, filed Jan. 31, 2017, entitled "Systems and Methods for Inferring Genetic Ancestry from Low-Coverage Genomic Data", the disclosure of each of which is incorporated herein by reference.

BACKGROUND

Patients and study subjects may report their race and/or ethnicity in accordance with guidelines set forth for clinical care or research. For example, institutions such as the American College of Medical Genetics and Genomics and the American Congress of Obstetricians and Gynecologists have guidelines for genetic screening to distinguish between people of Mediterranean, Ashkenazi Jewish, African, and South-East Asian descent. Many studies follow guidelines from the United States Office of Management and Budget, which specifies the use of racial categories including White, Black or African American, American Indian or Alaska Native, Asian, native Hawaiian, or Other Pacific Islander.

However, self-reported race or ethnicity may fail to convey all relevant underlying genetic information. For example, self-reported ethnicity may be inaccurate and/or imprecise (e.g., by failing to convey the extent of genetic admixture). Such inaccuracies and imprecisions may mask relevant attributes in a subject such as disease risk. Moreover, these inaccuracies and imprecisions may be expected to increase as coupling patterns indicate increased diversity in future generations.

Conventional techniques may attempt to estimate individual ancestry from genetic data. Unfortunately, these techniques may (i) rely on genotyping and/or sequencing data that is expensive to procure, (ii) rely on computationally expensive approaches, and/or (iii) may produce unreliable results. Accordingly, the instant disclosure identifies and addresses a need for additional and improved systems and methods for inferring genetic ancestry from low-coverage genomic data.

SUMMARY

The appended claims may serve as a summary of the invention.

BRIEF DESCRIPTION OF THE DRAWINGS

The accompanying drawings illustrate a number of example embodiments and are a part of the specification. Together with the following description, these drawings demonstrate and explain various principles of the instant disclosure.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the instant disclosure covers all modifications, equivalents, and alternatives falling within the scope of the appended claims.

DETAILED DESCRIPTION OF EXAMPLE EMBODIMENTS

The present disclosure is generally directed to systems and methods for inferring genetic ancestry from low-coverage genomic data. As will be explained in greater detail below, by analyzing genetic ancestry in terms of expected dosage, the systems and methods described herein may allow for uncertainty in genotype information and provide an accurate representation of admixture. In addition, in some examples, the systems and methods described herein may make use of raw sequencing data (e.g., reads rather than called and/or estimated genotypes). Furthermore, in some examples, these systems and methods may reduce computational expense and/or improve genetic ancestry analysis by comparing a sample against a reference panel (rather than, e.g., including the sample in the reference panel and analyzing the entire set). In some examples, the systems and methods described herein may make use of off-target sequencing data (e.g., obtained for a primary purpose other than determining genetic ancestry), thereby potentially facilitating genetic ancestry analysis without requiring separately acquired data. Generally, the systems and methods described herein may improve the precision and/or accuracy of genetic ancestry analysis; facilitate genetic ancestry analysis with incomplete, low-fidelity, and/or low-cost data; and/or reduce the computational cost of determining genetic ancestry.

Figure 1:
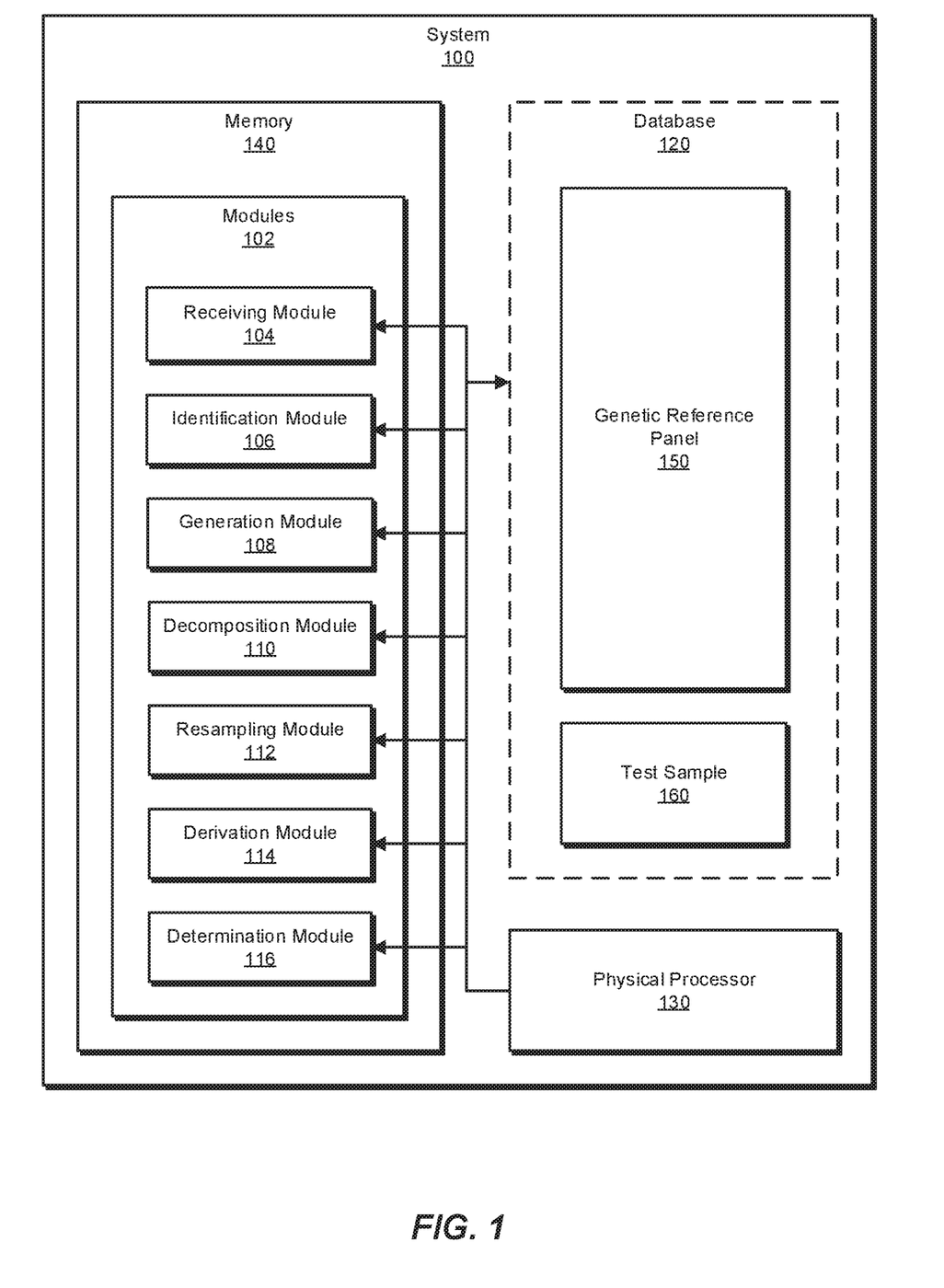
FIG. 1 is a block diagram of an example system for inferring genetic ancestry from low-coverage genomic data.
Figure 2:
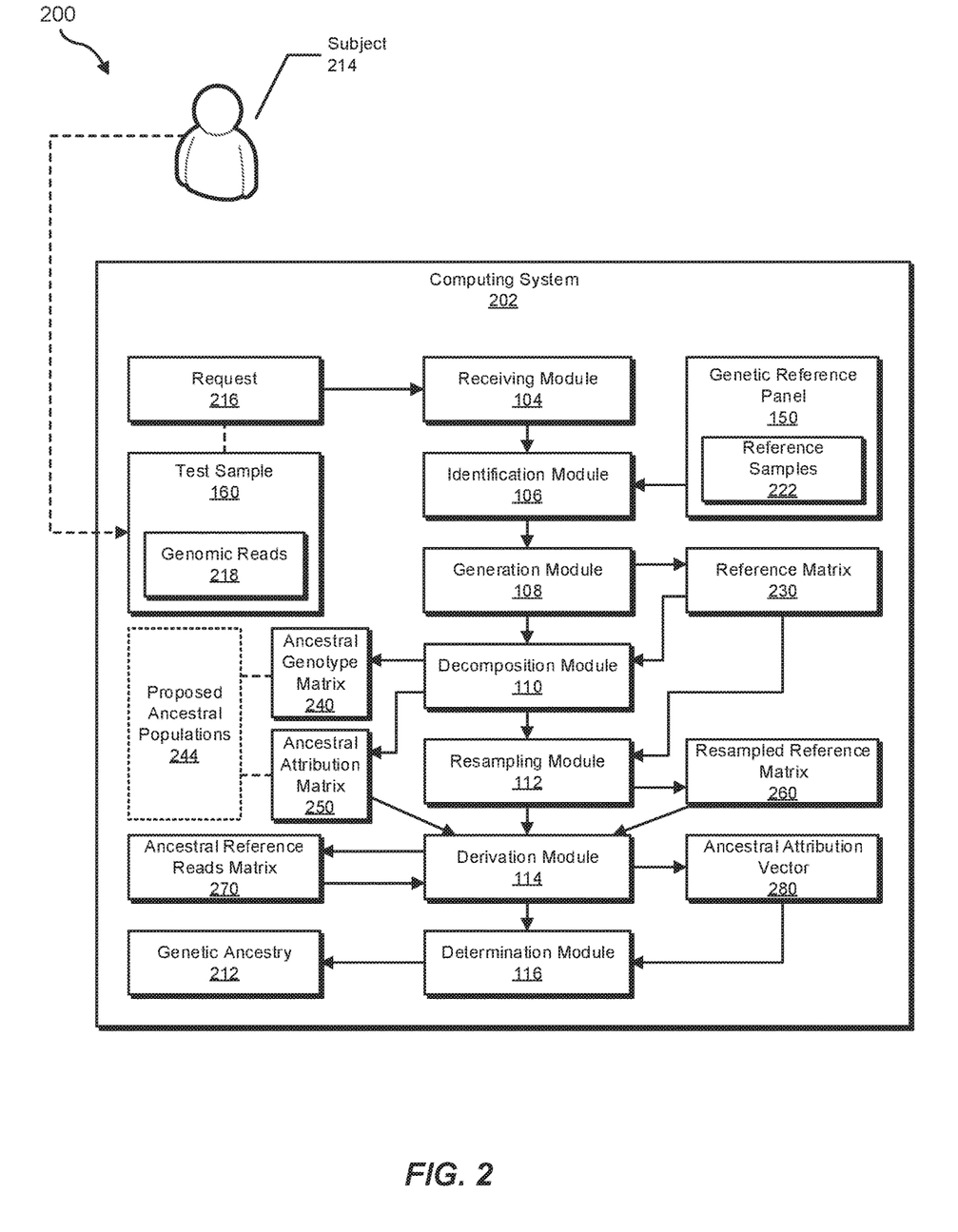
FIG. 2 is a block diagram of an additional example system for inferring genetic ancestry from low-coverage genomic data.

The following will provide, with reference to FIGS. 1-2, detailed descriptions of example systems for inferring genetic ancestry from low-coverage genomic data. Detailed descriptions of corresponding computer-implemented methods will also be provided in connection with FIG. 3. In addition, detailed descriptions of an example computing system implementing one or more of the embodiments described herein will be provided in connection with FIG. 6.

FIG. 1 is a block diagram of example system 100 for inferring genetic ancestry from low-coverage genomic data. As illustrated in this figure, example system 100 may include one or more modules 102 for performing one or more tasks. For example, and as will be explained in greater detail below, example system 100 may include a receiving module 104 that receives a request to determine a genetic ancestry of a subject given a test sample of the subject that includes a plurality of genomic reads from the subject. Example system 100 may additionally include an identification module 106 that identifies a genetic reference panel that includes a plurality of reference samples, each reference sample including, for each given locus of the plurality of loci, a dosage at the given locus. Example system 100 may also include a generation module 108 that generates a reference matrix representing the genetic reference panel, the reference matrix including a dimension that indicates the plurality of reference samples and a dimension that indicates the plurality of loci, where each cell of the reference matrix indicates a dosage for a given reference sample at a given locus. Example system 100 may additionally include a decomposition module 110 that decomposes the reference matrix via non-negative matrix factorization into an ancestral genotype matrix describing expected genotypes of a plurality of proposed ancestral populations and an ancestral attribution matrix attributing descent from one or more of the plurality of proposed ancestral populations to each of the plurality of reference samples. Example system 100 may also include a resampling module 112 that resamples the reference matrix to generate a resampled reference matrix, each cell of the resampled reference matrix indicating a projected number of alternate reads at a target locus if a sequencing depth at the target locus equaled the sequencing depth of the target locus in the test sample. Example system 100 may additionally include a derivation module 114 that (i) derives an ancestral alternate reads matrix that, when multiplied with the ancestral attribution matrix, approximates the resampled reference matrix and (ii) derives an ancestral attribution vector that, when multiplied with the ancestral alternate reads matrix, approximates a vector representing the test sample. Example system 100 may also include a determination module 116 that determines the genetic ancestry of the subject based on the ancestral attribution vector. Although illustrated as separate elements, one or more of modules 102 in FIG. 1 may represent portions of a single module or application.

In certain embodiments, one or more of modules 102 in FIG. 1 may represent one or more software applications or programs that, when executed by a computing device, may cause the computing device to perform one or more tasks. For example, and as will be described in greater detail below, one or more of modules 102 may represent software modules stored and configured to run on one or more computing devices, such as the devices illustrated in FIG. 2 (e.g., computing system 202) and/or computing system 610 in FIG. 6. One or more of modules 102 in FIG. 1 may also represent all or portions of one or more special-purpose computers configured to perform one or more tasks.

As illustrated in FIG. 1, example system 100 may also include one or more databases, such as database 120. In one example, database 120 may be configured to store a genetic reference panel 150 and/or a test sample 160.

Database 120 may represent portions of a single database or computing device or a plurality of databases or computing devices. For example, database 120 may represent a portion of computing system 202 in FIG. 2 and/or computing system 610 in FIG. 6. Alternatively, database 120 in FIG. 1 may represent one or more physically separate devices capable of being accessed by a computing device, such as computing system 202 in FIG. 2 and/or computing system 610 in FIG. 6.

Example system 100 in FIG. 1 may be implemented in a variety of ways. For example, all or a portion of example system 100 may represent portions of example system 200 in FIG. 2. As shown in FIG. 2, system 200 may include a computing device 202. In one example, computing device 202 may be programmed with one or more of modules 102 and/or may store all or a portion of the data in database 120.

In one embodiment, one or more of modules 102 from FIG. 1 may, when executed by at least one processor of computing device 202, enable computing device 202 to infer genetic ancestry from low-coverage genomic data. For example, and as will be described in greater detail below, one or more of modules 102 may cause computing device 202 to infer genetic ancestry from low-coverage genomic data. For example, and as will be described in greater detail below, receiving module 104 may receive a request 216 to determine a genetic ancestry 212 of a subject 214 given a test sample 160 of subject 214 that includes genomic reads 218 from subject 214. Identification module 106 may identify a genetic reference panel 150 that includes reference samples 222, each reference sample including, for each given locus of the plurality of loci, a dosage at the given locus. Generation module 108 may generate a reference matrix 230 representing genetic reference panel 150, reference matrix 230 including a dimension that indicates reference samples 222 and a dimension that indicates the plurality of loci, where each cell of reference matrix 230 indicates a dosage for a given reference sample at a given locus. Decomposition module 110 may decompose reference matrix 230 via non-negative matrix factorization into an ancestral genotype matrix 240 describing expected genotypes of proposed ancestral populations 244 and an ancestral attribution matrix 250 attributing descent from one or more of proposed ancestral populations 244 to each of reference samples 222. Resampling module 112 may resample reference matrix 230 to generate a resampled reference matrix 260, each cell of resampled reference matrix 260 indicating a projected number of alternate reads at a target locus if a sequencing depth at the target locus equaled the sequencing depth of the target locus in test sample 160. Derivation module 114 may derive an ancestral alternate reads matrix 270 that, when multiplied with ancestral attribution matrix 250, approximates resampled reference matrix 260. Derivation module 114 may derive an ancestral attribution vector 280 that, when multiplied with ancestral alternate reads matrix 270, approximates a vector representing test sample 160. Determination module 116 may determine genetic ancestry 212 of subject 214 based on ancestral attribution vector 280 (and, in some examples, based on ancestral attribution matrix 250).

Computing device 202 generally represents any type or form of computing device capable of reading computer-executable instructions. Examples of computing device 202 include, without limitation, workstations, desktops, servers, laptops, tablets, distributed computation systems, cellular phones, Personal Digital Assistants (PDAs), multimedia players, embedded systems, wearable devices (e.g., smart watches, smart glasses, etc.), gaming consoles, combinations of one or more of the same, example computing system 610 in FIG. 6, or any other suitable computing device.

Figure 3:
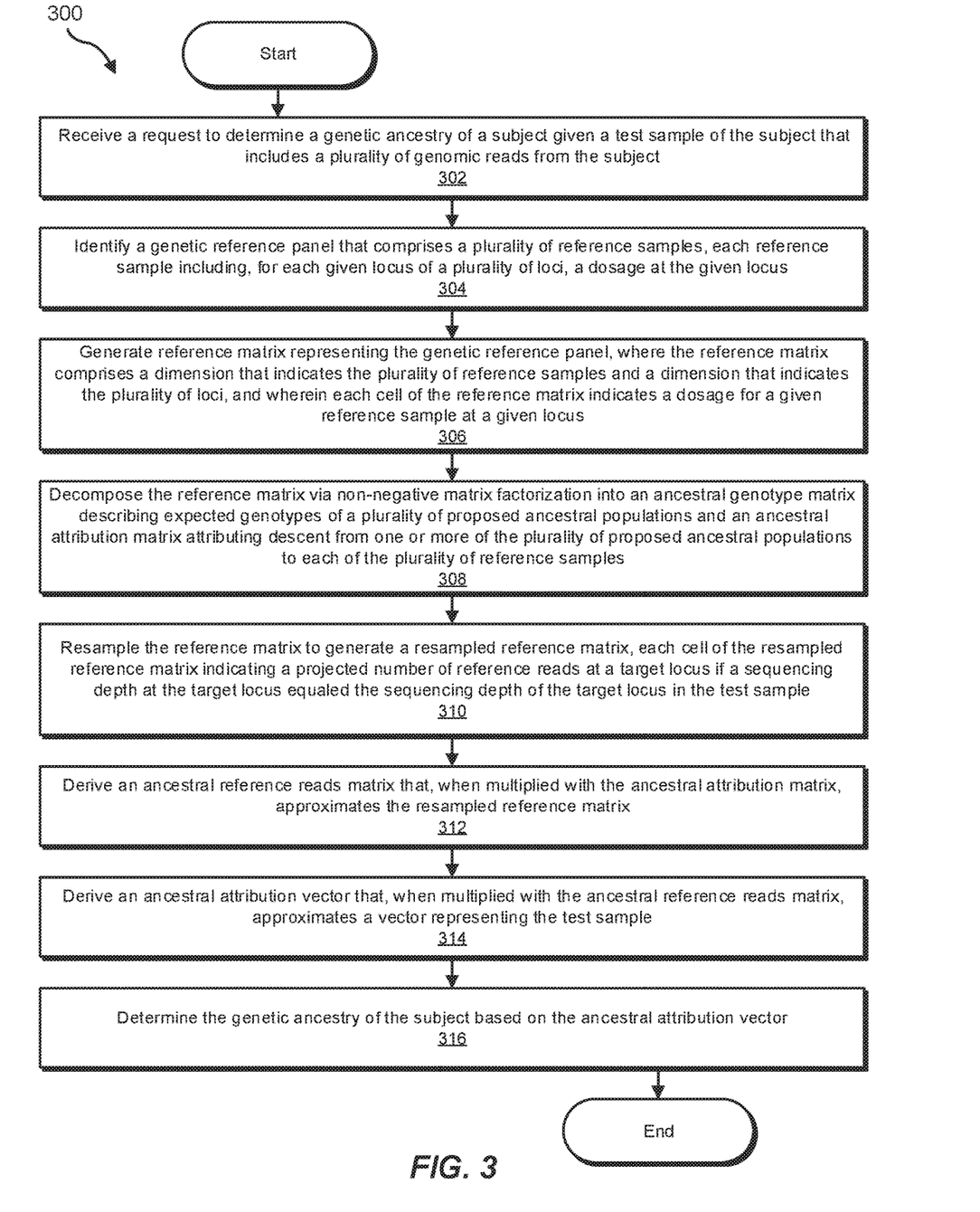
FIG. 3 is a flow diagram of an example method for inferring genetic ancestry from low-coverage genomic data.

FIG. 3 is a flow diagram of an example computer-implemented method 300 for inferring genetic ancestry from low-coverage genomic data. The steps shown in FIG. 3 may be performed by any suitable computer-executable code and/or computing system. In some embodiments, the steps shown in FIG. 3 may be performed by one or more of the components of system 100 in FIG. 1, system 200 in FIG. 2 and/or computing system 610 in FIG. 6.

As illustrated in FIG. 3, at step 302, one or more of the systems described herein may receive a request to determine a genetic ancestry of a subject given a test sample of the subject that may include a plurality of genomic reads from the subject. For example, receiving module 104 may, as part of computing device 202 in FIG. 2, receive request 216 to determine genetic ancestry 212 of subject 214 given test sample 160 of subject 214 that may include genomic reads 218 from subject 214.

The term "genetic ancestry," as used herein, may refer to any categorization, classification, description, and/or characterization of the contribution of one or more ancestral populations to the genome of a subject. In some examples, the term "genetic ancestry" may indicate information that may correspond to and/or stand in place of racial and/or ethnic classifications.

The term "subject," as used herein, generally refers to a person from whom genetic information may be derived. The systems and methods described herein may enable the efficient and effective determination of the genetic ancestry of a subject even, in some examples, where the genetic information derived from the subject is sparse, low-fidelity, and/or off-target.

The term "test sample," as used herein, generally refers to genetic information derived from a subject (e.g., from one or more genomic reads). The term "genomic read," as used herein, generally refers to any information from an attempt to discern genetic data at a locus within a genome. The test sample may be produced in any of a variety of ways. For example, the test sample may be derived from a sequencing procedure. Additionally or alternatively, the test sample may be derived from a genotyping procedure. In some examples, a high-throughput sequencing procedure may produce the plurality of genomic reads. In some examples, the test sample may be derived from an ultra-low coverage next-generation sequencing procedure. For example, the sequencing depth of the test sample may fall below 1×, below 0.1×, below 0.01×, and/or below 0.001×. In one example, the high-throughput sequencing (or next-generation sequencing) procedure may include a targeted sequencing procedure and the plurality of genomic reads may include off-target genomic reads. In some examples, the test sample may have originally been derived for use in a test other than testing for genetic ancestry. For example, the test sample may have been derived from short-read next generation sequencing procedures targeting regions of interest for carrier screening. Because the systems and methods described herein may successfully determine genetic ancestry based on uncertain, low-coverage, and/or low-fidelity data, the test sample may nevertheless be suitable for determining genetic ancestry. In some examples, the test sample may include unphased data. Additionally or alternatively, the test sample may include phased data.

In some examples, the plurality of genomic reads may include information indicating a likelihood of correctness for the plurality of genomic reads. For example, the plurality of genetic reads may include a number of reads at each locus and the results of the reads and associated sequencing quality metrics (e.g., two high-quality reads indicating a reference allele at the locus and one low quality read indicating an alternate allele at a locus where the subject genetically matches the reference).

In some examples, receiving module 104 may apply one or more quality filters to the test sample. For example, receiving module 104 may apply a read mapping quality filter to the test sample. Additionally or alternatively, receiving module 104 may apply a base quality score filter to the test sample.

Receiving module 104 may receive the request to determine the genetic ancestry of the subject in any suitable manner. For example, receiving module 104 may receive the request by receiving the test sample as input. Additionally or alternatively, receiving module 104 may receive the request by identifying a configuration option (e.g., associated with the test sample) indicating that the test sample is subject to analysis for genetic ancestry.

Returning to FIG. 3, at step 304, one or more of the systems described herein may identify a genetic reference panel that may include a plurality of reference samples, each reference sample including, for each given locus of the plurality of loci, a dosage at the given locus. For example, identification module 106 may, as part of computing device 202 in FIG. 2, identify genetic reference panel 150 that may include reference samples 222, each reference sample including, for each given locus of the plurality of loci, a dosage at the given locus.

The term "genetic reference panel," as used herein, generally refers to any dataset of genetic information derived from multiple subjects. For example, the genetic reference panel may include a number of reference samples, each reference sample containing genetic information for a corresponding person at a number of loci. In some examples, the genetic reference panel may include dosage information for various individuals at various loci. In some examples, the genetic reference panel may include metadata associated with the reference samples describing the corresponding subject. For example, the metadata may identify one or more populations of the subjects.

The term "locus," as used herein, generally refers to a genomic position of a gene and/or genetic marker. In some examples, a locus may be biallelic (e.g., showing either a reference allele or an alternate allele). However, while examples provided herein may focus on biallelic sites, in some examples three or more alleles may be found at a given locus. Accordingly, in some examples the systems and methods described herein may use virtual loci to describe genomic information. For example, a locus with three alleles (e.g., a reference allele and two alternate alleles) may be treated as two virtual loci: one virtual locus for differentiating between the reference allele and the first alternate allele, and one virtual locus for differentiating between the reference allele and the second alternate allele.

The term "dosage," as used herein, generally refers to a value indicating a number of instances of an allele at a given locus. For example, at a locus within a pair of homologous chromosomes, the dosage value may be 0 (the allele does not appear at the locus on either chromosome), 1 (the allele appears at the locus on one chromosomes), or 2 (the allele appears at the locus on both chromosomes). In some examples, dosage values may be determined in relation to a reference genome. Thus, the reference panel may include dosage values that indicate how many alleles at a given locus for a given sample do not match the reference genome (the number of "alternate alleles"). Conversely, the reference panel may include dosage values that indicate how many alleles at a given locus for a given sample do match the reference genome (the number of "reference alleles"). In one example, the reference panel may include dosage values relative to the reference genome hg19.

As used herein, the term "allele" may refer to any relevant genetic variation at a locus. For example, the term "allele" may refer to a nucleotide variation at a locus. Additionally or alternatively, the term "allele" may refer to a number of short tandem repeats at a locus. In some examples, the term "allele" may refer to a copy number variation (e.g., duplications of a gene or cluster of genes, or deletion of an intergenic region).

Identification module 106 may identify any suitable genetic reference panel. For example, the genetic reference panel may include the Human Genome Diversity Project (HGDP) reference panel. Additionally or alternatively, the genetic reference panel may include the GEO (Gene Expression Omnibus) accession no. GSE23636 (e.g., to analyze genetic ancestry focusing on Ashkenazi Jews). In some examples, the genetic reference panel may include a subset of an existing reference panel (e.g., for computational efficiency). For example, the genetic reference panel may include every third sample of GSE23636.

Identification module 106 may identify the genetic reference panel in any suitable manner. For example, identification module 106 may identify the genetic reference panel by reading the genetic reference panel from a configured storage location.

In some examples, identification module 106 may complete an existing genetic reference panel and/or generate the genetic reference panel from an incomplete genetic reference panel. For example, identification module 106 may identify missing dosage data within the genetic reference panel. The missing dosage data may include dosage information present at corresponding loci for some of the plurality of reference samples but not all of the plurality of reference samples. Information module 106 may then impute the missing dosage data for incomplete reference samples without dosage information as a given locus based at least in part on observed correlations between the incomplete reference samples and reference samples with dosage information at the given locus. In some examples, information module 106 may impute the missing dosage data with reference samples from an additional dataset (e.g., from Haplotype Reference Consortium r1.1). In some examples, information module 106 may impute the missing dosage data by sending a request to an imputation service. For example, information module 106 may send a request for an imputation of the reference panel using Haplotype Reference Consortium r1.1, asserting that the population was mixed, and using the Eaglet algorithm for phasing. In some examples, identification module 106 may remove some sites from the reference panel. For example, identification module 106 may remove sites on the sex chromosomes, sites with an imputation $R^2$ below a predetermined threshold (e.g., less than or equal to 0.8), and or sites with a dosage-based estimated minor allele frequency of less than a predetermined threshold (e.g., less than 0.001, less than 0.002, etc.).

Returning to FIG. 3, at step 306, one or more of the systems described herein may generate a reference matrix representing the genetic reference panel, the reference matrix including a dimension that indicates the plurality of reference samples and a dimension that indicates the plurality of loci, where each cell of the reference matrix indicates a dosage for a given reference sample at a given locus. For example, generation module 108 may, as part of computing device 202 in FIG. 2, generate reference matrix 230 representing genetic reference panel 150, reference matrix 230 including a dimension that indicates reference samples 222 and a dimension that indicates the plurality of loci, where each cell of reference matrix 230 indicates a dosage for a given reference sample at a given locus.

The term "matrix," as used herein, generally refers to any data structure and/or arrangement of data that enables the performance of matrix operations. Accordingly, matrices may be implemented in the form of multi-dimensional arrays and/or any other data structure capable of representing a series of linear equations.

Generation module 108 may generate the reference matrix in any suitable manner. For example, generation module 108 may generate an L×N data structure X, where L is the number of loci represented within the reference matrix, N is the number of individual subjects represented within the reference matrix, and $X_{l,n}$ represents the dosage at the lth locus of the nth individual subject. While examples provided herein may focus on a consistent convention (e.g., the reference matrix as an L×N matrix rather than a N×L matrix), it may be appreciated that similar principles and techniques would apply if the dimensions of the matrices discussed herein were reversed.

In some examples, a subset of dosage values within the reference matrix may include probabilistic and continuous dosage values. For example, as mentioned earlier, the systems described herein (e.g., identification module 106 and/or generation module 108) may impute missing values to the reference panel. Accordingly, the imputed values may represent expected values, and the systems and methods described herein may preserve the expected values as probabilistic floating-point values (rather than, e.g., rounding to the nearest whole number). Thus, the reference matrix may include dosage values between 0 and 2, inclusive, some of which may be whole numbers (e.g., the dosage values present in the reference panels before imputation) and some of which may be non-whole real numbers (e.g., the imputed dosage values).

Figure 4:
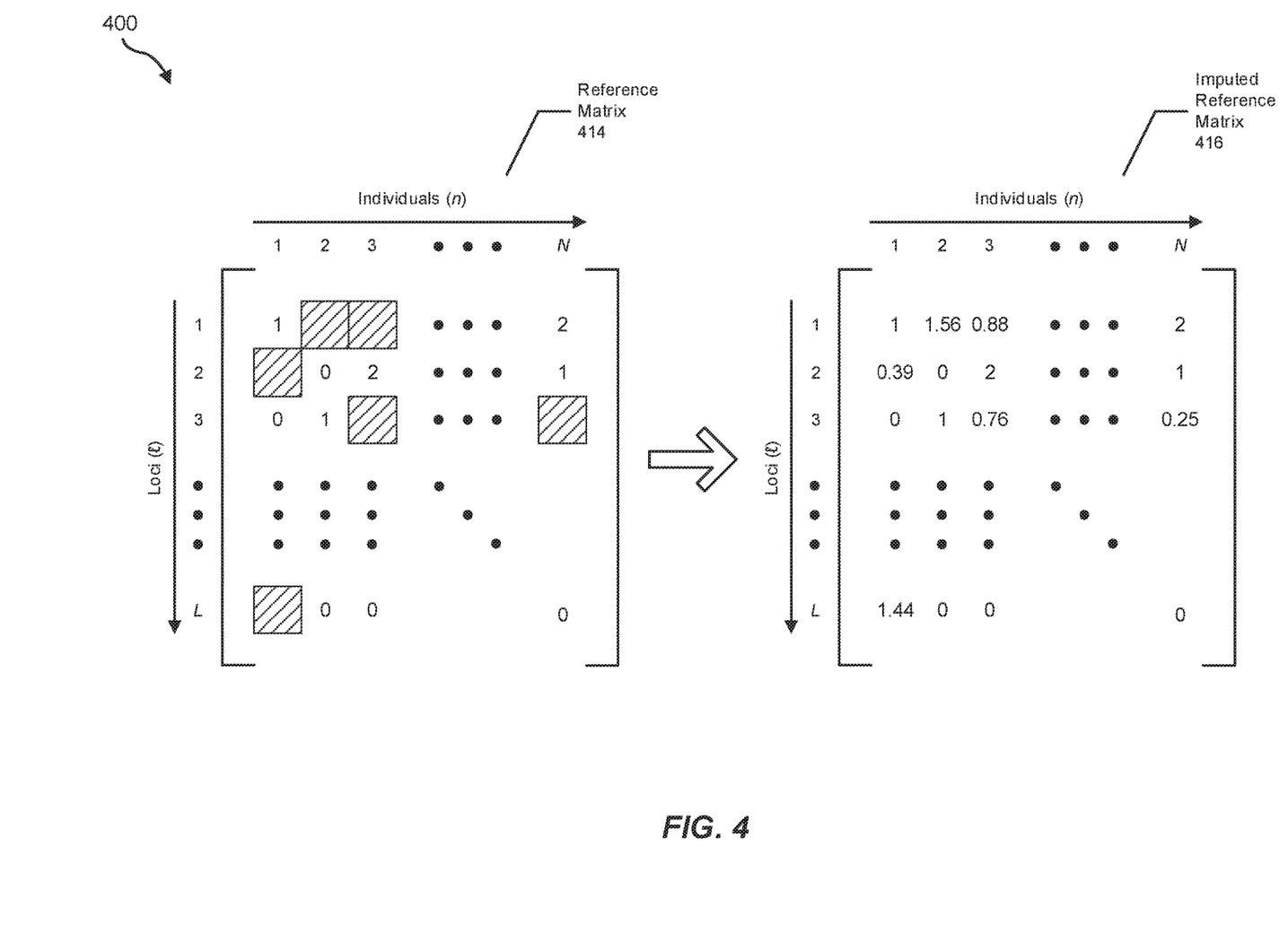
FIG. 4 is an illustration of an imputation of values within an example reference matrix.

FIG. 4 provides an illustration of an imputation 400. As shown in FIG. 4, a reference matrix 414 may be a L×N matrix with some dosage values (0, 1, or 2) and some missing values. Following imputation, an imputed reference matrix 416 may include the same dosage values as are present in reference matrix 414 and may also include imputed dosage values in place of the missing dosage values.

Returning to FIG. 3, at step 308, one or more of the systems described herein may decompose the reference matrix via non-negative matrix factorization into an ancestral genotype matrix describing expected genotypes of a plurality of proposed ancestral populations and an ancestral attribution matrix attributing descent from one or more of the plurality of proposed ancestral populations to each of the plurality of reference samples. For example, decomposition module 110 may, as part of computing device 202 in FIG. 2, decompose reference matrix 230 via non-negative matrix factorization into ancestral genotype matrix 240 describing expected genotypes of proposed ancestral populations 244 and ancestral attribution matrix 250 attributing descent from one or more of proposed ancestral populations 244 to each of reference samples 222.

The term "non-negative matrix factorization," as used herein, generally refers to any technique for factorizing a matrix into two matrices with no negative elements. In some examples, the term "non-negative matrix factorization" may refer to an approximate factorization (i.e., the product of the factor matrices approximating the factorized matrix without exactly equaling the factorized matrix).

The term "ancestral population," as used herein, generally refers to any posited genetically distinct group to which the genetics of a subject may be at least partly attributed. For example, the term "ancestral population" may refer to a hypothetical population with allele frequencies that are in Hardy-Weinberg equilibrium.

Decomposition module 110 may model the genome of each individual j as being derived in proportion $q_{k,j}$ from ancestral population k. Accordingly, the dosage at locus e would be represented according to Equation (1):

$$x_{l,j} = \sum_{k=1}^{K} g_{l,k} q_{k,j} \tag{1}$$

where K is the number of ancestral populations.

Thus, if $X_{ref}$ is the reference matrix, $G_{ref}$ is the ancestral genotype matrix, and $Q_{ref}$ is the ancestral attribution matrix, then the relationship between the matrices may be represented according to Equation (2):

$$X_{ref} = G_{ref} Q_{ref} \tag{2}$$

where $G_{ref}$ is an L×K matrix, L being the number of loci and K being the number of ancestral populations; and where $Q_{ref}$ is a K×N matrix, K being the number of ancestral populations and N being the number of individuals.

Thus, in some examples, the ancestral attribution matrix may attribute descent from one or more of the plurality of proposed ancestral populations to each of the plurality of reference samples by modeling each reference sample genome described by a corresponding reference sample within the plurality of reference samples as being derived in specified proportions from each of the plurality of proposed ancestral populations.

Decomposition module 110 may decompose the reference matrix in any of a variety of ways. In some examples, decomposition module 110 may constrain the decomposition of the reference matrix. For example, decomposition module 110 may constrain the decomposition of the reference matrix such that each value representing a proportion of descent from one of the plurality of proposed ancestral populations falls between zero and one, inclusive. Additionally or alternatively, decomposition module 110 may constrain the decomposition of the reference matrix such that a sum of values representing proportions of descent from each of the plurality of proposed ancestral populations equals one. In this manner, decomposition module 110 may produce a factorization according to the model described in Equation (1) above, where each individual is modeled as deriving a non-negative proportion of genetic information from a set of ancestral populations that account entirely for the genetic ancestry of the individual. In some examples, the matrix factorization may involve an iterative process. In these examples, decomposition module 110 may apply the two aforementioned constraints at each iteration.

In some examples, decomposition module 110 may constrain the decomposition of the reference matrix such that each value for a corresponding locus within the ancestral genotype matrix falls between zero and a ploidy of the corresponding locus, inclusive. For example, decomposition module 110 may constrain the decomposition of the reference matrix such that each value falls between zero and two, inclusive, for loci on autosomes.

In some examples, decomposition module 110 may decompose reference matrix by decomposing the transposition of the reference matrix. For example, decomposition module 110 may perform a non-negative matrix factorization according to Equation (3):

$$X^T_{ref} = Q^T_{ref} G^T_{ref} \tag{3}$$

In some examples, decomposition module 110 may decompose the reference matrix into the ancestral genotype matrix and the ancestral attribution matrix by constraining the decomposition of the reference matrix to toward sparseness of the ancestral genotype matrix. For example, decomposition module 110 may decompose the reference matrix while penalizing non-sparse ancestral genotype matrix candidates to a predetermined degree. In one example, decomposition module 110 may decompose the reference matrix while suppressing the Frobenius norm of the ancestral genotype matrix to a predetermined degree. In some examples, decomposition module 110 may decompose the reference matrix into the ancestral genotype matrix and the ancestral attribution matrix by constraining the decomposition of the reference matrix to toward sparseness of the ancestral attribution matrix. For example, decomposition module 110 may decompose the reference matrix while penalizing non-sparse ancestral attribution matrix candidates to a predetermined degree.

In one example, decomposition module 110 may decompose imputed reference panel combining the HGDP reference panel and the GSE23636 reference panel using the NIMFA library, with K=7 ancestral populations, q=0.1 (to control the sparseness of the $G_{ref}$ matrix), and β=0.001 (to control the sparseness of the $Q_{ref}$ matrix). In some examples, decomposition module 110 may halt an iterative factorization process of the imputed reference panel according to an error-minimization metric that describes error in the factorization and/or according to a resources metric that describes time and/or computing resources consumed in the factorization process.

Figure 5:
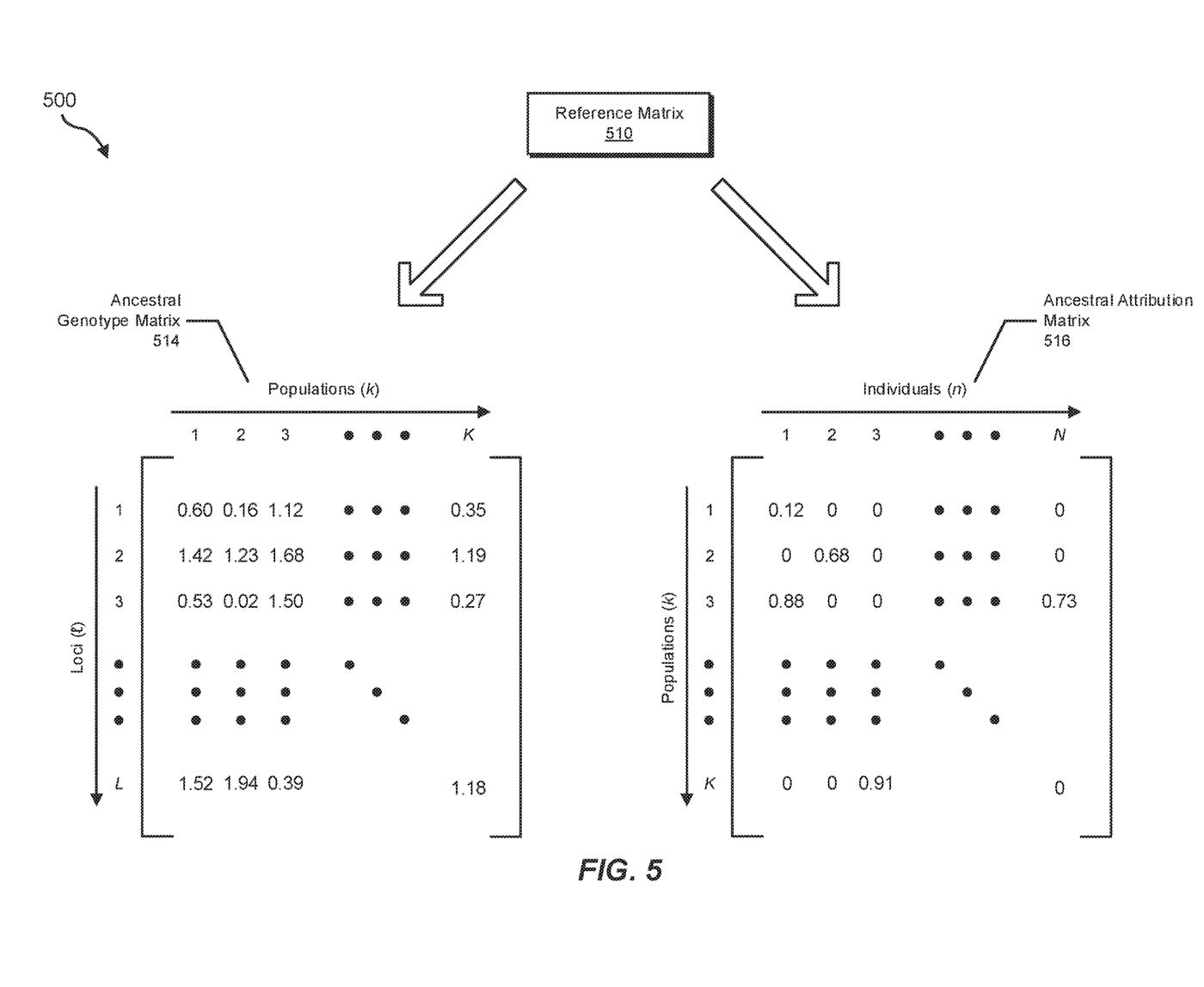
FIG. 5 is an illustration of a decomposition of an example reference matrix.

FIG. 5 illustrates an example decomposition 500 of a reference matrix 510 into an ancestral genotype matrix 514 and an ancestral attribution matrix 516. As shown in FIG. 5, ancestral genotype matrix 514 may include expected dosage values for each of K populations at each of L loci. Ancestral attribution matrix 516 may include proportions of genetic ancestry from each of K populations for each of N individuals. As may be appreciated, the K populations represented in FIG. 5 may correspond to proposed ancestral populations 244 in FIG. 2.

Returning to FIG. 3, at step 310, one or more of the systems described herein may resample the reference matrix to generate a resampled reference matrix, each cell of the resampled reference matrix indicating a projected number of alternate reads at a target locus if a sequencing depth at the target locus equaled the sequencing depth of the target locus in the test sample. For example, resampling module 112 may, as part of computing device 202 in FIG. 2, resample reference matrix 230 to generate resampled reference matrix 260, each cell of resampled reference matrix 260 indicating a projected number of alternate reads at a target locus if a sequencing depth at the target locus equaled the sequencing depth of the target locus in test sample 160.

Similar to the reference matrix, resampling module 112 may produce the resampled reference matrix as an L×N data structure $X_s$, where L is the number of loci represented within the resampled reference matrix, N is the number of individual subjects represented within the resampled reference matrix, and $X_{s_{l,n}}$ represents the projected number of alternate reads at the lth locus of the nth individual subject.

The term "alternate read," as used herein, generally refers to a read corresponding to an alternate allele (e.g., rather than a reference allele). In some examples, the resampled reference matrix may represent the projected number of alternate reads as a value corresponding to the projected number of alternate reads. In some examples, resampling module 112 may represent the projected number of alternate reads in terms of the projected number of reference reads. In some examples, resampling module 112 may normalize the data by representing the projected number of alternate reads as a fraction of the total number of reads at the locus.

The phrase "sequencing depth," as it relates to a given locus, generally refers to the number of reads at the given locus (such that a larger number of reads corresponds to a greater "depth").

Resampling module 112 may resample the reference matrix in any suitable manner. For example, resampling module 112 may resample the reference matrix to generate the resampled reference matrix by performing a plurality of simulations of genomic sequencing operations for individuals within the genetic reference panel. In some examples, resampling module 112 may determine the projected number of alternate reads for an individual at a locus by calculating an expected number of alternate reads (e.g., based on the probability of erroneous reads). Additionally or alternatively, resampling module 112 may determine the projected number of alternate reads for an individual at a locus by simulating reads with a probability of error and observing the results of the simulation.

In some examples, resampling module 112 may generate the resampled reference matrix further by normalizing the resampled reference matrix by, for each locus represented within the resampled reference matrix, calculating a standard deviation of values within the resampled reference matrix describing the locus across the reference samples and dividing each value within the resampled reference matrix describing the locus by the standard deviation.

In some examples, as will be discussed in greater detail below, resampling module 112 may include a vector representing the test sample (e.g., that describes a number of alternate reads for the subject at each locus represented within the resampled reference matrix).

Returning to FIG. 3, at step 312, one or more of the systems described herein may derive an ancestral alternate reads matrix that, when multiplied with the ancestral attribution matrix, approximates the resampled reference matrix. For example, derivation module 114 may, as part of computing device 202 in FIG. 2, derive ancestral alternate reads matrix 270 that, when multiplied with ancestral attribution matrix 250, approximates resampled reference matrix 260.

Derivation module 114 may derive the ancestral alternate reads matrix in any suitable manner. For example, the decomposition of the resampled reference matrix may be given as shown in Equation (4):

$$X_s = G_s Q_s \qquad (4)$$

Where $G_s$ is the ancestral alternate reads matrix. However, instead of decomposing $X_s$ to produce the ancestral alternate reads matrix, derivation module 114 may take advantage of the equality $Q_s = Q_{ref}$ (because resampling the reference matrix would not impact the ancestral nature of the reference samples). Thus, derivation module 114 may avoid a computationally expensive decomposition. Instead, derivation module 114 may solve for $G_s$ in the equation $X_s = G_s Q_{ref}$. In some examples, derivation module 114 may derive the ancestral alternate reads matrix by approximating the ancestral alternate reads matrix using a least squares approximation based on the ancestral attribution matrix and the resampled reference matrix. For example, derivation module 114 may approximate $G_s$ as shown in Equation (5):

$$\hat{G}_s = X_s Q^T_{ref}(Q_{ref}Q^T_{ref})^{-1} \qquad (5)$$

Returning to FIG. 3, at step 314, one or more of the systems described herein may derive an ancestral attribution vector that, when multiplied with the ancestral alternate reads matrix, approximates a vector representing the test sample. For example, derivation module 114 may, as part of computing device 202 in FIG. 2, derive ancestral attribution vector 280 that, when multiplied with ancestral alternate reads matrix 270, approximates a vector representing test sample 160.

The ancestral attribution vector may include proportions of descent for the subject attributable to each of the proposed ancestral populations. Accordingly, the relationship between the test sample, the ancestral alternate reads matrix, and the ancestral attribution vector may be represented as shown in Equation (6):

$$x_s = G_s q_s \qquad (6)$$

where $x_s$ is a vector of the number of reads mapping to the reference at each observed locus of the test sample of the subject, $G_s$ is the ancestral attribution matrix (which may be substituted with $\hat{G}_s$, the approximation of $G_s$), and $q_s$ is the ancestral attribution vector. Thus, derivation module 114 may approximate the ancestral attribution vector based on the ancestral alternate reads matrix and the vector representing the test sample. For example, derivation module 114 may derive the ancestral attribution vector by approximating the ancestral attribution vector using a least squares approximation based on the ancestral alternate reads matrix and the vector representing the test sample. For example, derivation module 114 may approximate the ancestral attribution vector as shown in Equation (7):

$$q_s = (\hat{G}_s^T \hat{G}_s)^{-1} \hat{G}_s^T x_s \qquad (7)$$

In some examples, derivation module 114 may derive the ancestral attribution vector by approximating the ancestral attribution vector, based on the ancestral alternate reads matrix and the vector representing the test sample, such that the ancestral attribution vector is constrained to include values between zero and one, inclusive, and to result in the sum of the values of the ancestral attribution vector to be one.

In some examples, derivation module 114 may normalize each given value representing a given locus in the vector representing the test sample by calculating a standard deviation corresponding to the given locus, the standard deviation corresponding to the given locus comprising all values within the resampled reference matrix corresponding to the given locus (e.g., using the values within the resampled reference matrix before normalization), and dividing the given value representing the given locus in the vector representing the test sample by the standard deviation corresponding to the given locus.

In some examples, the systems described herein (e.g., derivation module 114 and determination module 116) may reuse the results of the decomposition of the reference matrix to calculate ancestral attribution vectors for multiple samples, such that the decomposition of the reference matrix is performed once but used to determine the genetic ancestry of many subjects. Because the ancestral attribution vectors may be approximated efficiently and effectively given the techniques discussed above, the systems described herein may thereby enable rapid, low-cost processing of requests to determine genetic ancestry.

In some examples, one or more of the systems described herein (e.g., derivation module 114 and/or decomposition module 110) may derive the ancestral attribution vector by decomposing a version of the resampled reference matrix that includes the vector representing the test sample. For example, derivation module 114 may extend the resampled reference matrix to include the vector representing the test sample. Derivation module 114 may then decompose the resampled reference matrix into the ancestral alternate reads matrix and the ancestral attribution matrix. In this example, the resulting ancestral attribution matrix would include the ancestral attribution vector that corresponds to the vector representing the test sample. Accordingly, derivation module 114 may extract the ancestral attribution vector from the ancestral attribution matrix.

Returning to FIG. 3, at step 316, one or more of the systems described herein may determine the genetic ancestry of the subject based on the ancestral attribution vector. For example, determination module 116 may, as part of computing device 202 in FIG. 2, determine genetic ancestry 212 of subject 214 based on ancestral attribution vector 280.

Determination module 116 may determine the genetic ancestry of the subject based on the ancestral attribution vector in any suitable manner. For example, determination module 116 may interpret each value of the ancestral attribution vector as the proportion of genetic ancestry of the subject to attribute to the corresponding ancestral population.

In some examples, determination module 116 may model individuals as vectors in a K-dimensional space, where K is the number of proposed ancestral populations. In some examples, determination module 116 may perform this modelling according to the ancestral population information derived with the foregoing techniques (i.e., fast, sparse non-negative matrix factorization). In some examples, determination module 116 may alternatively analyze the reference panel samples according to a principal component analysis.

In some examples, determination module 116 may model individuals as vectors in a K-dimensional space by generating a plurality of reference clusters from the plurality of reference samples located within a multi-dimensional space, where each dimension within the multi-dimensional space corresponds to a proportion of descent from one of the plurality of proposed ancestral populations. In some examples, determination module 116 may analyze reference samples within the reference panel for genetic ancestry with depth profiles generated algorithmically and/or drawn from the mean observed depth distribution of analyzed individuals.

Reference populations may be modeled as following K-dimensional multivariate normal distributions. Accordingly, in some examples, determination module 116 may iteratively merge cluster pairs within the plurality of reference clusters until a distance between a closest cluster pair within the plurality of reference cluster exceeds a predetermined threshold. For example, determination module 116 may iteratively merge populations into clusters if the Mahalanobis distance between population clusters is within the $99.99^{th}$ percentile of the Chi distribution with K-1 degrees of freedom, choosing the closest pair each iteration.

In some examples, determination module 116 may also define a plurality of clines connecting each possible pair of reference clusters within the plurality of reference clusters, each cline within the plurality of clines describing a line connecting a pair of reference clusters within the plurality of reference clusters and representing a population composed of an admixture of two reference populations. For example, a cline in K-dimensional genetic ancestry space may be defined as variation along the line connecting the mean vectors $\mu_A$ and $\mu_B$ of two reference populations A and B, defined by the vector $\mu_B - \mu_A$. The populations A and B may be models as having Gaussian covariances cov(A) and cov(B) in genetic ancestry space. Accordingly, the ancestry vector q may be modeled as shown in Equation (8):

$$q = f\mu_A + (1-f)\mu_B + \varepsilon \qquad (8)$$

where f is the admixture coefficient showing the proportion of admixture shared with population A and $\varepsilon$ is an error term.

Accordingly, in some examples determination module 116 may calculate an estimate for where a sample would have been in the absence of noise orthogonal to the cline according to Equation (9):

$$C = \frac{(q-\mu_A)^T(\mu_B-\mu_A)}{(\mu_B-\mu_A)^T(\mu_B-\mu_A)}(\mu_B-\mu_A) + \mu_A \qquad (9)$$

Determination module 116 may then calculate an estimation off according to Equation (10):

$$\hat{f} = 1 - \frac{\|C-\mu_A\|}{\|\mu_B-\mu_A\|} \qquad (10)$$

Determination module 116 may then derive the covariance matrix for the error according to Equation (11):

$$\mathrm{cov}(\varepsilon|q) = \mathrm{cov}(q-C|q) = \mathrm{cov}(C) = \hat{f}^2\,\mathrm{cov}(A) + (1-\hat{f})^2\,\mathrm{cov}(B) \qquad (11)$$

Determination module 116 may determine that the likelihood of membership of the test sample to a cline is proportional to the prior membership probability times the probability density of the error term at q, related to how far from the cline the test sample was with respect to the expected variation. Thus, determination module 116 may determine a membership of the subject to a cline within the plurality of clines based at least in part on a probability that the ancestral attribution vector pertains to the cline.

In some examples, determination module 116 may associate ethnic labels with the reference clusters, and thereby may determine the genetic ancestry of the subject in terms of an admixture of the ethnic labels associated with the reference clusters. For example, determination module 116 may determine that the subject pertains to a cline connecting a cluster labeled as "sub-Saharan African" and a cluster labeled as "European." Accordingly, determination module 116 may determine the genetic ancestry of the subject by determining that the genetic ancestry of the subject is a specified admixture of sub-Saharan African and European ancestry.

In some examples, determination module 116 may determine that the subject pertains to a cluster within the plurality of reference clusters rather than to a cline connecting two clusters if f=1 is more likely than the scenario given by $\hat{f}$. In this case, determination module 116 may use $\hat{f}$ from the most likely cline as the admixture coefficient estimate for the appropriate cluster but may assign $1-\hat{f}$ of the genetic ancestry of the subject to the "Other" category.

In some examples, determination module 116 may determine that the genetic ancestry of the subject is represented by an admixture of three or more reference populations. For example, determination module 116 may generate simulated admixtures by combining the ancestral attribution vectors of different reference samples (e.g., determination module 116 may generate one simulated admixture by taking the ancestral attribution vector of a sample from an African population and weighting it by 16/64, taking the ancestral attribution vector of a sample from a European population and weighting it by 32/64, and taking the ancestral attribution vector of a sample from a Native American population and weighting it by 16/64, and then summing the weighted values to get a simulated reference sample with 25% African ancestry, 50% European ancestry, and 25% Native American ancestry). Determination module 116 may then compare the ancestral attribution vector of the test sample to the simulated ancestral attribution vectors and choose the closest simulated ancestral attribution vector. Determination module 116 may then attribute the admixture of the closest simulated ancestral attribution vector to the subject. In some examples, determination module 116 may determine the closest simulated ancestral attribution vector via a K-dimensional tree. In some examples, determination module 116 may identify a set of closest simulated ancestral attribution vectors and apply an ensemble decision-making technique (e.g., majority voting, averaging, etc.) to the set of closest simulated ancestral attribution vectors to attribute an admixture of populations to the subject.

In some examples, one or more of the systems described herein may repeat one or more of the steps described herein to refine the determination of the genetic ancestry of the subject. For example, if a proportion of the genetic ancestry of a subject is attributed to a population, the systems described herein may analyze the genetic ancestry of the subject using a subpanel directed to that population as the genetic reference panel. As an example, determination module 116 may determine that 90% of the genetic ancestry of a subject is attributable to a "European or Middle Eastern" population and that 10% of the genetic ancestry of the subject is attributable to a Pacific Islander population. The systems described herein may then analyze the genetic ancestry of the subject using a subpanel restricted to the "European or Middle Eastern" population and determine that the genetic ancestry of the subject relative to the subpanel is 60% attributable to a European population and 40% attributable to a Middle Eastern population. Accordingly, determination module 116 may determine that the genetic ancestry of the subject may be represented as an admixture of three populations: 54% European (90%*60%), 36% Middle Eastern (90%*40%), and 10% Pacific Islander.

As another example, determination module 116 may determine, based on an initial determination of genetic ancestry of a subject (or of a group of subjects), that a reference population is irrelevant (e.g., that the genetic ancestry of the subject attributable to the reference population falls below a minimum threshold). Accordingly, determination module 116 may (i) perform the analysis of the genetic ancestry of the subject again, excluding the irrelevant reference population from the genetic reference panel, and/or (ii) exclude the irrelevant population from the genetic reference panel from the analysis performed for related subjects (e.g., subjects from the same region). In this manner, the systems described herein may both increase precision in genetic ancestry determinations (e.g., by freeing a dimension or identifying relevant populations) and/or may reduce the computational complexity of determining genetic ancestry.

In some examples, one or more of the systems described herein may generate a report regarding the subject based at least in part on the determined genetic ancestry of the subject. For example, determination module 116 may generate a report regarding the subject based at least in part on the determined genetic ancestry of the subject. For example, determination module 116 may generate a report to the subject that describes the genetic ancestry of the subject. Additionally or alternatively, determination module 116 may generate a report to a doctor of the subject and/or to a researcher conducting a study that includes the subject.

In some examples, determination module 116 may report on a result within a carrier screening procedure based at least in part on the determined genetic ancestry of the subject. For example, a screening procedure (e.g., a carrier screening procedure, an inherited cancer screening procedure) may mask results based on ethnicity. However, determination module 116 may, upon determining the genetic ancestry of the subject, transmit an instruction to unmask results that are relevant in light of the genetic ancestry of the subject. For example, a set of screening procedures may include sequencing a set of genes. However, one or more particular screening procedures within the set may include masking a subset of the results. In some examples, the systems described herein may, in light of the genetic ancestry of the subject, unmask results for the subject that would otherwise be masked.

Figure 6:
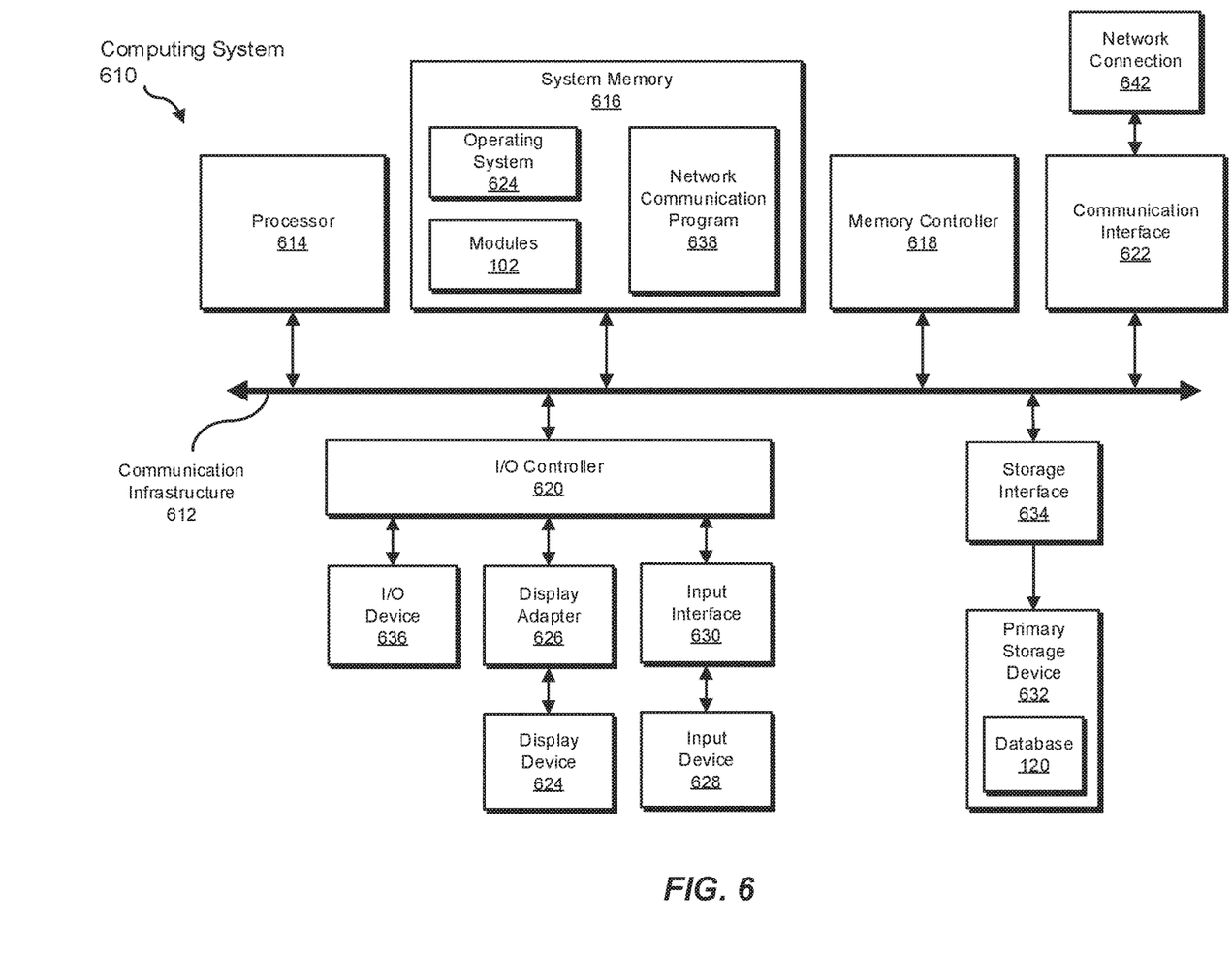
FIG. 6 is a block diagram of an example computing system capable of implementing one or more of the embodiments described and/or illustrated herein.

FIG. 6 is a block diagram of an example computing system 610 capable of implementing one or more of the embodiments described and/or illustrated herein. For example, all or a portion of computing system 610 may perform and/or be a means for performing, either alone or in combination with other elements, one or more of the steps described herein (such as one or more of the steps illustrated in FIG. 3). All or a portion of computing system 610 may also perform and/or be a means for performing any other steps, methods, or processes described and/or illustrated herein.

Computing system 610 broadly represents any single or multi-processor computing device or system capable of executing computer-readable instructions. Examples of computing system 610 include, without limitation, workstations, laptops, client-side terminals, servers, distributed computing systems, handheld devices, or any other computing system or device. In its most basic configuration, computing system 610 may include at least one processor 614 and a system memory 616.

Processor 614 generally represents any type or form of physical processing unit (e.g., a hardware-implemented central processing unit) capable of processing data or interpreting and executing instructions. In certain embodiments, processor 614 may receive instructions from a software application or module. These instructions may cause processor 614 to perform the functions of one or more of the example embodiments described and/or illustrated herein.

System memory 616 generally represents any type or form of volatile or non-volatile storage device or medium capable of storing data and/or other computer-readable instructions. Examples of system memory 616 include, without limitation, Random Access Memory (RAM), Read Only Memory (ROM), flash memory, or any other suitable memory device. Although not required, in certain embodiments computing system 610 may include both a volatile memory unit (such as, for example, system memory 616) and a non-volatile storage device (such as, for example, primary storage device 632, as described in detail below). In one example, one or more of modules 102 from FIG. 1 may be loaded into system memory 616.

In some examples, system memory 616 may store and/or load an operating system 624 for execution by processor 614. In one example, operating system 624 may include and/or represent software that manages computer hardware and software resources and/or provides common services to computer programs and/or applications on computing system 610. Examples of operating system 824 include, without limitation, LINUX, JUNOS, MICROSOFT WINDOWS, WINDOWS MOBILE, MAC OS, APPLE'S 10S, UNIX, GOOGLE CHROME OS, GOOGLE'S ANDROID, SOLARIS, variations of one or more of the same, and/or any other suitable operating system.

In certain embodiments, example computing system 610 may also include one or more components or elements in addition to processor 614 and system memory 616. For example, as illustrated in FIG. 6, computing system 610 may include a memory controller 618, an Input/Output (I/O) controller 620, and a communication interface 622, each of which may be interconnected via a communication infrastructure 612. Communication infrastructure 612 generally represents any type or form of infrastructure capable of facilitating communication between one or more components of a computing device. Examples of communication infrastructure 612 include, without limitation, a communication bus (such as an Industry Standard Architecture (ISA), Peripheral Component Interconnect (PCI), PCI Express (PCIe), or similar bus) and a network.

Memory controller 618 generally represents any type or form of device capable of handling memory or data or controlling communication between one or more components of computing system 610. For example, in certain embodiments memory controller 618 may control communication between processor 614, system memory 616, and I/O controller 620 via communication infrastructure 612.

I/O controller 620 generally represents any type or form of module capable of coordinating and/or controlling the input and output functions of a computing device. For example, in certain embodiments I/O controller 620 may control or facilitate transfer of data between one or more elements of computing system 610, such as processor 614, system memory 616, communication interface 622, display adapter 626, input interface 630, and storage interface 634.

As illustrated in FIG. 6, computing system 610 may also include at least one display device 624 coupled to I/O controller 620 via a display adapter 626. Display device 624 generally represents any type or form of device capable of visually displaying information forwarded by display adapter 626. Similarly, display adapter 626 generally represents any type or form of device configured to forward graphics, text, and other data from communication infrastructure 612 (or from a frame buffer, as known in the art) for display on display device 624.

As illustrated in FIG. 6, example computing system 610 may also include at least one input device 628 coupled to I/O controller 620 via an input interface 630. Input device 628 generally represents any type or form of input device capable of providing input, either computer or human generated, to example computing system 610. Examples of input device 628 include, without limitation, a keyboard, a pointing device, a speech recognition device, variations or combinations of one or more of the same, and/or any other input device.

Additionally or alternatively, example computing system 610 may include additional I/O devices. For example, example computing system 610 may include I/O device 636. In this example, I/O device 636 may include and/or represent a user interface that facilitates human interaction with computing system 610. Examples of I/O device 636 include, without limitation, a computer mouse, a keyboard, a monitor, a printer, a modem, a camera, a scanner, a microphone, a touchscreen device, variations or combinations of one or more of the same, and/or any other I/O device.

Communication interface 622 broadly represents any type or form of communication device or adapter capable of facilitating communication between example computing system 610 and one or more additional devices. For example, in certain embodiments communication interface 622 may facilitate communication between computing system 610 and a private or public network including additional computing systems. Examples of communication interface 622 include, without limitation, a wired network interface (such as a network interface card), a wireless network interface (such as a wireless network interface card), a modem, and any other suitable interface. In at least one embodiment, communication interface 622 may provide a direct connection to a remote server via a direct link to a network, such as the Internet. Communication interface 622 may also indirectly provide such a connection through, for example, a local area network (such as an Ethernet network), a personal area network, a telephone or cable network, a cellular telephone connection, a satellite data connection, or any other suitable connection.

In certain embodiments, communication interface 622 may also represent a host adapter configured to facilitate communication between computing system 610 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 622 may also allow computing system 610 to engage in distributed or remote computing. For example, communication interface 622 may receive instructions from a remote device or send instructions to a remote device for execution.

In some examples, system memory 616 may store and/or load a network communication program 638 for execution by processor 614. In one example, network communication program 638 may include and/or represent software that enables computing system 610 to establish a network connection 642 with another computing system (not illustrated in FIG. 6) and/or communicate with the other computing system by way of communication interface 622. In this example, network communication program 638 may direct the flow of outgoing traffic that is sent to the other computing system via network connection 642. Additionally or alternatively, network communication program 638 may direct the processing of incoming traffic that is received from the other computing system via network connection 642 in connection with processor 614.

Although not illustrated in this way in FIG. 6, network communication program 638 may alternatively be stored and/or loaded in communication interface 622. For example, network communication program 638 may include and/or represent at least a portion of software and/or firmware that is executed by a processor and/or Application Specific Integrated Circuit (ASIC) incorporated in communication interface 622.

As illustrated in FIG. 6, example computing system 610 may also include a primary storage device 632 coupled to communication infrastructure 612 via a storage interface 634. Storage device 632 generally represent any type or form of storage device or medium capable of storing data and/or other computer-readable instructions. For example, storage device 632 may be a magnetic disk drive (e.g., a so-called hard drive), a solid state drive, a floppy disk drive, a magnetic tape drive, an optical disk drive, a flash drive, or the like. Storage interface 634 generally represents any type or form of interface or device for transferring data between storage device 632 and other components of computing system 610. In one example, one or more of the elements included in database 120 from FIG. 1 may be stored and/or loaded in primary storage device 632.

In certain embodiments, storage device 632 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage device 632 may also include other similar structures or devices for allowing computer software, data, or other computer-readable instructions to be loaded into computing system 610. For example, storage device 632 may be configured to read and write software, data, or other computer-readable information. Storage device 632 may also be a part of computing system 610 or may be a separate device accessed through other interface systems.

Many other devices or subsystems may be connected to computing system 610. Conversely, all of the components and devices illustrated in FIG. 6 need not be present to practice the embodiments described and/or illustrated herein. The devices and subsystems referenced above may also be interconnected in different ways from that shown in FIG. 6. Computing system 610 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 610. All or a portion of the computer program stored on the computer-readable medium may then be stored in system memory 616 and/or various portions of storage device 632. When executed by processor 614, a computer program loaded into computing system 610 may cause processor 614 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 610 may be configured as an Application Specific Integrated Circuit (ASIC) adapted to implement one or more of the example embodiments disclosed herein.

As detailed above, computing system 610 may perform and/or be a means for performing, either alone or in combination with other elements, one or more steps of an example method for inferring genetic ancestry from low-coverage genomic data.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 100 in FIG. 1 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

According to various embodiments, all or a portion of example system 100 in FIG. 1 may be implemented within a virtual environment. For example, the modules and/or data described herein may reside and/or execute within a virtual machine. As used herein, the phrase "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the phrase "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 100 in FIG. 1 may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

In addition, one or more of the modules described herein may transform data, physical devices, and/or representations of physical devices from one form to another. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A computer-implemented method for a genetic screening procedure for a patient of a healthcare provider, at least a portion of the method being performed by a computing device comprising at least one processor, the method comprising:
    deriving genetic data for the patient using a low-coverage next-generation sequencing procedure, the genomic data comprising raw sequencing data and a plurality of loci corresponding to genetic markers in a genome of the patient;
    identifying, based on the genomic data of the patient, a genetic reference dataset that (i) comprises reference genomic reads for subjects other than the patient, and that (ii) comprises, for each subject, dosages at reference loci corresponding to the plurality of loci in the genomic data of the patient;
    generating a reference matrix representing the genetic reference dataset, wherein the reference matrix comprises a first dimension corresponding to the subjects and a second dimension corresponding to the reference loci, and wherein each cell of the reference matrix indicates a dosage for a subject at a locus in the reference loci;
    generating, based on the reference matrix, an ancestral attribution matrix attributing descent from one or more of a plurality of proposed ancestral populations to each of the subjects;
    deriving, based on the ancestral attribution matrix, an ancestral attribution vector of the patient that comprises a proportion of descent for each subject attributable to each of the plurality of proposed ancestral populations, wherein deriving the ancestral attribution vector of the patient comprises generating a plurality of simulated ancestral attribution vectors, and identifying one or more of the simulated ancestral attribution vectors to attribute an admixture of populations to the patient by a decision making technique with a K-dimensional tree; and
    determining a genetic ancestry of the patient based on the identified one or more ancestral attribution vectors.

2. The computer-implemented method of claim 1, further comprising applying a sequencing procedure to a biological sample from the patient to derive the genomic data, wherein the sequencing procedure is a high-throughput sequencing procedure.

3. The computer-implemented method of claim 2, wherein:
    the high-throughput sequencing procedure comprises a targeted sequencing procedure; and
    the genomic data comprise off-target genomic reads.

4. The computer-implemented method of claim 2, wherein the genomic data comprise information indicating a likelihood of correctness for genomic reads in the genomic data of the patient.

5. The computer-implemented method of claim 1, wherein identifying the genetic reference dataset comprises:
    identifying missing dosage data within the genetic reference dataset, wherein the missing dosage data comprises dosage information present at corresponding reference loci for some but not all of the subjects; and
    imputing the missing dosage data at a given locus based at least in part on observed correlations between the reference genetic reads for subjects without dosage information at the given locus and reference genetic reads for subjects with dosage information at the given locus.

6. The computer-implemented method of claim 1, wherein identifying the genetic reference dataset comprises imputing dosage data to the genetic reference dataset based at least in part on an additional genetic dataset.

7. The computer-implemented method of claim 1, wherein a subset of dosages within the reference matrix comprises probabilistic and continuous dosage values.

8. The computer-implemented method of claim 1, wherein generating the ancestral attribution matrix comprises modeling each reference genome as being derived in specified proportions from each of the plurality of proposed ancestral populations.

9. The computer-implemented method of claim 8, wherein generating the ancestral attribution matrix based on the reference matrix comprises constraining the generation of the ancestral attribution matrix such that:
    each value representing a proportion of descent from one of the plurality of proposed ancestral populations falls between zero and one; and
    for reference genetic reads of each subject, a sum of values representing proportions of descent from each of the plurality of proposed ancestral populations equals one.

10. The computer-implemented method of claim 1, wherein generating the ancestral attribution matrix comprises penalizing non-sparse ancestral attribution matrix candidates to a predetermined degree.

11. The computer-implemented method of claim 1, further comprising deriving an ancestral alternate reads matrix based on the ancestral attribution matrix, wherein deriving the ancestral alternate reads matrix comprises using a least squares approximation based on the ancestral attribution matrix and the reference matrix.

12. The computer-implemented method of claim 1, wherein deriving the ancestral attribution vector comprises approximating the ancestral attribution vector using a least squares approximation based on an ancestral alternate reads matrix and the ancestral attribution matrix, the ancestral alternative reads matrix being based on the ancestral attribution matrix and the reference matrix.

13. The computer-implemented method of claim 1, wherein deriving the ancestral attribution vector comprises approximating the ancestral attribution vector such that:
   the ancestral attribution vector is constrained to including values between zero and one; and
   a summation of values within the ancestral attribution vector is constrained to be one.

14. The computer-implemented method of claim 1, further comprising generating a plurality of reference clusters from the reference genetic reads located within a multi-dimensional space, wherein each dimension within the multi-dimensional space corresponds to the proportion of descent from one of the plurality of proposed ancestral populations.

15. The computer-implemented method of claim 14, further comprising iteratively merging cluster pairs within the plurality of reference clusters until a distance between a closest cluster pair within the plurality of reference cluster exceeds a predetermined threshold.

16. The computer-implemented method of claim 14, further comprising defining a plurality of dines connecting each possible pair of reference clusters within the plurality of reference clusters, each cline within the plurality of dines describing a line connecting a pair of reference clusters within the plurality of reference clusters and representing a population composed of an admixture of two reference populations.

17. The computer-implemented method of claim 16, wherein determining the genetic ancestry of the patient subject further comprises determining a membership of the patient to a dine within the plurality of dines based at least in part on a probability that the ancestral attribution vector pertains to the dine.

18. The computer-implemented method of claim 1, wherein the sequencing procedure has a sequencing depth of less than 0.1x.

19. The computer-implemented method of claim 1, wherein the genetic screening procedure is a carrier screening procedure or an inherited cancer screening procedure.

20. A computing system for inferring genetic ancestry from low-coverage genomic data for a genetic screening procedure, the computing system comprising:
   at least one processor;
   a receiving module, stored in computer-readable non-transitory memory, that receives, via the at least one processor, through an input device or a communication interface, low-coverage genomic data of a patient, the genomic data comprising raw sequencing data and a plurality of loci corresponding to genetic markers;
   an identification module, stored in the computer-readable non-transitory memory, that identifies, via the at least one processor, based on the genomic data of the patient, a genetic reference dataset that (i) comprises reference genomic reads for subjects other than the patient, and that (ii) comprises, for each subject, dosages at reference loci corresponding to the plurality of loci in the genomic data of the patient;
   a generation module, stored in the computer-readable non-transitory memory, that generates, via the at least one processor, a reference matrix representing the genetic reference dataset, wherein the reference matrix comprises a first dimension corresponding to the subjects and a second dimension corresponding to the reference loci, and wherein each cell of the reference matrix indicates a dosage for a subject at a locus in the reference loci;
   a decomposition module, stored in the computer-readable non-transitory memory, that generates, via the at least one processor, based on the reference matrix, an ancestral attribution matrix attributing descent from one or more of a plurality of proposed ancestral populations to each of the subjects;
   a derivation module, stored in the computer-readable non-transitory memory, that derives, via the at least one processor, based on the ancestral attribution matrix, an ancestral attribution vector of the patient that comprises a proportion of descent for each subject attributable to each of the plurality of proposed ancestral populations, wherein deriving the ancestral attribution vector of the patient comprises generating a plurality of simulated ancestral attribution vectors, and identifying one or more of the simulated ancestral attribution vectors to attribute an admixture of populations to the patient by a decision making technique with a K-dimensional tree; and
   a determination module, stored in the computer-readable non-transitory memory, that determines, via the at least one processor, the genetic ancestry of the patient based on the identified one or more ancestral attribution vectors.

21. A non-transitory computer-readable medium comprising one or more computer-readable instructions that, when executed by at least one processor of a computing device, cause the computing device to:
   receive, through an input device or a communication interface of the computing device, low-coverage genomic data of a patient identified as having an ethnicity in the computing device, the genomic data comprising raw sequencing data and a plurality of loci corresponding to genetic markers;
   identify, based on the genomic data, a genetic reference dataset that (i) comprises reference genomic reads for subjects other than the patient, and that (ii) comprises, for each subject, dosages at reference loci corresponding to the plurality of loci in the genomic data of the patient;
   generate a reference matrix representing the genetic reference dataset, wherein the reference matrix includes a first dimension corresponding to the subjects and a second dimension corresponding to the reference loci, and wherein each cell of the reference matrix indicates a dosage for a subject at a locus in the reference loci;
   generate, based on the reference matrix, an ancestral attribution matrix attributing descent from one or more of a plurality of proposed ancestral populations to each of the subjects;

derive, based on the ancestral attribution matrix, an ancestral attribution vector of the patient that comprises a proportion of descent for each subject attributable to each of the plurality of proposed ancestral populations, wherein deriving the ancestral attribution vector of the patient comprises generating a plurality of simulated ancestral attribution vectors, and identifying one or more of the simulated ancestral attribution vectors to attribute an admixture of populations to the patient by a decision making technique with a K-dimensional tree; and determine the genetic ancestry of the patient based on the identified one or more ancestral attribution vectors.

\* \* \* \* \*